United States Patent
Jensen

(10) Patent No.: US 10,463,579 B2
(45) Date of Patent: *Nov. 5, 2019

(54) REVERSIBLE DENTAL ADHESIVE

(71) Applicant: Steven D. Jensen, South Jordan, UT (US)

(72) Inventor: Steven D. Jensen, South Jordan, UT (US)

(73) Assignee: CAO Group, Inc., West Jordan, UT (US)

(*) Notice: Subject to any disclaimer, the term of this patent is extended or adjusted under 35 U.S.C. 154(b) by 0 days.

This patent is subject to a terminal disclaimer.

(21) Appl. No.: 15/424,187

(22) Filed: Feb. 3, 2017

(65) Prior Publication Data

US 2017/0143591 A1    May 25, 2017

Related U.S. Application Data

(63) Continuation of application No. 13/969,126.

(60) Provisional application No. 61/683,716, filed on Aug. 16, 2012, provisional application No. 61/800,372, filed on Mar. 15, 2013.

(51) Int. Cl.
*A61K 6/00* (2006.01)
*A61C 13/15* (2006.01)
*A61C 1/00* (2006.01)

(52) U.S. Cl.
CPC .......... *A61K 6/0058* (2013.01); *A61C 1/0046* (2013.01); *A61C 19/003* (2013.01); *A61K 6/0002* (2013.01); *A61K 6/0023* (2013.01); *A61K 6/0061* (2013.01); *A61K 6/0094* (2013.01)

(58) Field of Classification Search
CPC .. A61K 6/0094; A61K 6/0002; A61K 6/0061; A61C 1/0046; A61C 19/003
USPC .............. 250/492.1, 493.1, 504 R, 504 H
See application file for complete search history.

(56) References Cited

U.S. PATENT DOCUMENTS

| 4,907,965 A | 3/1990 | Martin |
| 9,597,264 B2 * | 3/2017 | Jensen ............... A61K 6/0094 |
| 2007/0142498 A1 * | 6/2007 | Brennan ............. A61K 6/0023 |
| | | 523/118 |
| 2012/0058453 A1 | 3/2012 | Jensen |

\* cited by examiner

*Primary Examiner* — Nicole M Ippolito

(57) ABSTRACT

A method of removing a dental adhesive may comprise locating the position of the dental adhesive, directing radiant energy into the dental adhesive causing the dental adhesive to weaken a bond formed with the dental adhesive, and breaking the bond by applying a suitable force to overcome the weakened bond. A dental adhesive may comprise a polymer and a dye or pigment, The dental adhesive may be formulated to cure to form a bond that is weakened in response to the dye or pigment absorbing radiant energy subsequent to curing.

7 Claims, No Drawings

REVERSIBLE DENTAL ADHESIVE

CROSS-REFERENCE TO RELATED APPLICATIONS

This application is a continuation application of U.S. application Ser. No. 13/969,126, filed on Aug. 16, 2013, which claims the benefit of U.S. Provisional Application No. 61/683,716, filed Aug. 16, 2012, and U.S. Provisional Application No. 61/800,372, filed on Mar. 15, 2013, the disclosure of each of which is incorporated herein by reference in its entirety.

TECHNICAL FIELD

The present disclosure relates to dental adhesives. In particular, the present disclosure relates to dental adhesives that are reversible or otherwise able to break the adhesive bond when the bond is no longer desired.

BACKGROUND OF THE INVENTION

In the contemporary dental office many types of adhesives, composites, cements, and other restorative resin systems are utilized daily. Most of these resin systems are designed to permanently repair or set into place a prefabricated prosthetic. Once placed, these restorative prosthetics must be busted/broken to be removed at a later time due to the fact the adhesive bond will not allow removal of the restorative prosthetic.

What is needed in the art are dental resin systems that are reversible, such that they can be purposefully destabilized and removed without breaking the prosthetic.

SUMMARY

A method of removing a dental adhesive may comprise locating the position of the dental adhesive, directing radiant energy into the dental adhesive causing the dental adhesive to weaken a bond formed with the dental adhesive, and breaking the bond by applying a suitable force to overcome the weakened bond.

A dental adhesive may comprise a polymer and a dye or pigment, The dental adhesive may be formulated to cure to form a bond that is weakened in response to the dye or pigment absorbing radiant energy subsequent to curing.

DETAILED DESCRIPTION

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

Example embodiments of the present invention include light curable or chemical curable materials to create an adhesive or adhesive system that is reversible in adhesive nature. In particular, embodiments of the present invention include adhesives that once cured form a strong bond. However, by introducing additional energy into the cured adhesive, the cured adhesive becomes degraded, destabilized and/or depolymerized such that the adhesive nature of the cured adhesive is reversed, allowing release of the bond.

Example embodiments of the present invention utilize light and chemical curable monomer/polymers to create a polymerizable resin or adhesive system that is reversibly destabilized/de-polymerized and or molten into a temporary or non-temporary degraded/weakened state.

In one example embodiment, a method of destabilization includes introducing laser energy that directly and precisely transfers energy to the polymerized resin wherein it is absorbed and turned into heat. The heat in turn causes the polymerized resin to undergo de-polymerization, degradation or simply melts the polymerized matrix sufficiently that it becomes weakened or enters a fluid state. In alternative embodiments, other methods of introducing energy can be used, for example heat blowers, heat elements, or other similar methods.

Once the resin system is in a weakened or molten state any dental prosthetic or appliance can be removed without applying excessive force that could break or alter said prosthetic or appliance. For example, once the adhesive system has absorbed a sufficient amount of energy, the adhesive properties of the systems are weakened to the point that a dental professional could easily remove the dental prosthetic.

One example of a reversible resin includes are monomers that form homopolymers without branching or cross-linking. The ideal monomer would consist of a light and chemical curable monomer that when polymerized forms a thermoplastic that melts at low temperature, preferably between 40 C and 70 C. Another example of reversible resins are monomers that are capable of de-polymerization and degradation when subjected to elevated temperatures, preferably between 40 C-70 C. Additional reversible resins are also contemplated such as light and chemical curable polymers capable of crosslinking/branching and co-polymerization, such that they retain the ability to degrade, de-polymerize and/or melt at an appropriate temperature.

In the laboratory we have found a unique means to weaken/degrade a polymer incorporating plasticizers. The system comprises a monomer(s), a curing agent, a radiant energy absorbent pigment/dye and a plasticizer(s). When incorporated into a light curable formulation we could create a reversible polymeric system. The liquid formulation when irradiated with the appropriate light would initiate polymerization and form the expected rigid polymer matrix. The plasticizer(s) can be added in amounts that can vary the rigidity and flexibility of the polymer.

When the cured polymer is irradiated with a laser attuned to the radiant energy dye/pigment the light is absorbed and converted into heat that begins to heat the polymer matrix locally. The plasticizer becomes heated and expands and stresses the polymeric confinement such that it eventually begins to crack/break (stress propagation) the polymeric crystalline matrix on a microscopic level. The polymer when heated becomes permanently weakened and is easily fractured by the addition of external forces such as bending/flexing the polymer. Rapid heating of the polymer actually fractures the polymer such that the polymer breaks apart or forms a snowflake type fractures in the polymer.

The plasticizer may perform multiple functions within the polymeric matrix. First, when plasticizer becomes heated it becomes either molten or in a more fluidic state which acts as a lubricant and/or solvent such that it is more capable of reducing friction within the polymeric network; therefore the polymer becomes more pliable. Second, the plasticizer expands and applies internal pressure inside the polymeric matrix stressing the bonds making them weaker. If sufficient heat is applied the expansion becomes great enough to actually sever those bonds and the polymer begins to fracture into a permanently weakened state.

The laser and absorbent dye and pigment are only a means to communicate heat to the plasticized polymeric matrix, other means of adding heat to said polymer are also possible, such as a heated wand or bag that is placed over the polymer and heated through conduction. A heat lamp would also deliver the required heat; in effect any device capable of delivering heat to the polymer would complete the system.

Suitable plasticizers include but are not limited to: dibutyl phthalate, triethyl citrate, triacetin, sucrose diacetate hexaisobutyrate and any other useful plasticizer.

Chemical cure resin systems are mixed composition systems. Usually incorporates a part A and a part B, that when mixed together uniting the polymerization catalyst results in subsequent polymerization.

Light cure resin systems are light sensitive compositions that contain catalysts that initiate polymerization upon receiving radiant energy such as light.

The preferred types of resins are acrylics/methacrylics because they are compatible with almost all contemporary dental resin systems currently on the market.

Resins such as epoxy, urethanes and other useful resins are also contemplated.

Useful acrylic resins are polyethylene glycol methacrylates, polypropylene glycol methacrylates, Diurethane dimethacrylate, hydroxyethyl methacrylate, bis-phenol A diglycidyl dimethacrylate, triethylenegycol dimethacrylate, isodecyl methacrylate, Bisphenol A ethoxylate dimethacrylates, Poly(ethylene glycol) methyl ether methacrylate, and many other useful methacrylic resins.

Light cure systems incorporate a tertiary amine such as dimethyl aminoethyl methacrylate and a photo initiator such as camphorquinone.

Chemical cure systems usually consist of benzoyl peroxide in part A, and dimethyl para toluidine in part B, that when mixed together initiate free radical polymerization.

Absorption dyes are designed to significantly absorb at known frequencies/wavelengths. These dyes are classified by their specific frequencies where their maximum absorption or lambda maximum is determined. Many absorption dyes have multiple Lambda Max. Absorption dyes in raw material form come in many colors covering much of the color spectrum. In many applications the physical color of the raw dye is not an issue, since the application is indifferent. There are some applications where colors are very important and the selection is imperative to the system. As an example, dental restorative resin systems are designed to replace or cement missing portions of a tooth or teeth. A red or blue tinted resin would not be aesthetically pleasing to the patient as it would be obvious to strangers, since it is generally accepted that teeth should be shades of white.

This patent utilizes specific dyes, and resin systems to create an aesthetically pleasing resin/monomer/polymer system that is capable of significant absorption of radiant energy at specific wavelengths.

More specifically the present invention targets wavelengths in ranges of 380 nm-450 nm. More broad ranges of 400 nm-615 nm. Most broad ranges of 100 nm-700 nm.

The ideal wavelength is about 405 nm, or any radiant energy source capable of producing visible violet light. Less ideal are radiant energy sources that produce UV, blue and green light; though are definitely within the scope of this patent. The physical color of raw absorption dyes usually counter-correspond to the wavelengths of the radiant light source. Blue light is usually absorbed by yellow dyes. Green light is usually absorbed by red dyes. UV light is usually absorbed by white to transparent dyes. Violet light is usually absorbed by yellow, white, and translucent dyes.

Violet light is ideal, because the corresponding absorption dyes are the most aesthetically adaptable into a resin system. The best to worst colors for dyes/pigments are:
Translucent/transparent/clear
White
Off white
Light yellow
Dark yellow
Light brown
Dark brown All other colors such as blues, greens and reds are very difficult to make aesthetically pleasing; it requires great skill to add additional colors to offset these primary colors; such as adding red and green together to produce a more useful color like brown.

The absorption dyes associated with UV light are as ideal as those for violet light; namely translucent/transparent, white dyes. UV light is second to violet light only because in some cases UV light is physiologically hazardous and extra precautions must be in place for its use.

The preferred light of the present invention is violet light having a wavelength range of about 380 nm-450 nm. The 405 nm laser is an ideal radiant energy device of the present invention. More specifically, the 405 nm diode laser is preferred since its cost and compact size combine to create a more affordable laser.

Violet light is preferred because of its capability to match radiant energy absorbent dyes of aesthetic colors most preferably transparent, translucent, and or white in physical color. There are multiple white/translucent dyes or pigments that absorb violet light such as: 4,4"-(1,2-ethenediyl)bis-1,1'-biphenyl, and 4,4'"-bis[(2-butyloctyl)oxy]-1,1':4',1":4",1'"-quaterphenyl and 2-[1,1'-biphenyl]-4-yl-6-phenyl-benzoxazole and 3,5,3"",5""-tetra-t-butyl-p-sexiphenyl and 2-(1-naphthyl)-5-phenyl-oxazole and 3,5,3 . . . , 5 . . . -tetra-t-butyl-p-quinquephenyl and any other useful dyes or pigments capable of absorbing violet light.

Dyes and pigments that are physically yellow also absorb violet light such as: 2,2"-([1,1'-biphenyl]-4.4'-diyldi-2,1-ethenediyl)bis-benzenesulfonic acid disodium salt and/or any other dye or pigment capable of absorbing violet light.

Many white/translucent/crystalline dyes and pigments are also absorbed by UV light, these dyes are also very capable of creating an aesthetic resin system; many dyes and pigments listed above will also absorb UV light. Since UV light may present a physiological hazard it is not as preferred as violet light.

There are many radiant energy absorbent yellow dyes and pigments that absorb blue light. Therefore blue light is an excellent radiant energy source to irradiated aesthetic resin systems containing yellow dyes. Yellow dyes are not as good as white/translucent/crystalline dyes and pigments, but are still capable of creating an aesthetic resin system.

There are some violet light absorbent dyes that are slightly yellow and/or light yellow in physical color whose absorbance efficiency exceeds about 70%. Dyes that are highly light absorbent at a desired wavelength are preferred over those that have less light absorbency, because you need to add less dye to the formulation for an equal effect; regardless of the physical color of the dye. It is much easier to make an aesthetic resin composition with a highly absorbent dye since it requires a smaller quantity of dye in the first place; the ideal highly light absorbent dye would require such a small amount of dye that the color change in the resin composition would be insignificant.

Violet light absorbent dyes that are yellow in physical color and absorb greater than about 70% light are ideal dyes for manufacturing clear/transparent/white aesthetic resin compositions.

The absorbance characteristics of all dyes can be selected to impart a desired absorption effect. The absorbance effect can be adjusted between localized and diffuse characteristics. For a localized effect the highly radiant energy absorbent dye is selected such that most of the absorbance is concentrated at the surface and very little is transmitted into deeper layers. This is beneficial when you want radiant energy limited to the surface or near surface and want to avoid transmission to substrates that lie underneath. The same localized effect can be manufactured by low absorptive dyes as well; simply by adding more dye to the formulation to compensate for the lack of absorption, this is not preferred because it is more difficult to make an aesthetic composition; unless the dye is of the appropriate color to begin with.

For a diffuse effect a highly absorptive radiant energy dye(s) can be added in ever-smaller quantities to a point that the spaces between the dyes(s) become great enough to allow the desired diffusion of radiant energy. Alternatively, a low radiant energy absorptive dye(s) can also be selected to produce a customized composition that allows light to pass into deeper layers (sub-surface) of the composition and into substrates underneath if desired.

These radiant energy absorbent dyes and pigments are dissolved, mixed, and/or blended together with monomer(s) and/or Co-monomer(s) to create a light absorbent resin system. Additional catalysts, initiators and photoinitiators are added to the resin formulation to create a polymerizable radiant energy absorbent resin matrix/system; such that when polymerization is initialized by chemical, photochemical and or thermal means, it forms into a hardened physical state.

In both the monomeric state and the polymeric state the formulation is capable of absorbing radiant energy of a specific wavelength in order to effectuate a change within the formulation itself, such as thermal, chemical, chemical reactions, and/or physical or material changes or modifications. An example of such use is a radiant energy absorbent dye dissolved into a polymerizable monomer system that is polymerized into a hardened state photochemically; the polymerized polymer is then irradiated with sufficient radiant energy of the wavelength that matches the incorporated dye thereby heating the polymer sufficiently that it either heats, fractures, cracks, melts or becomes permanently or temporarily weakened. Many uses are possible with different systems dependent on the desired outcome.

Chemical cure resin systems are mixed composition systems. Usually incorporates a part A and a part B, that when mixed together uniting the polymerization catalyst results in subsequent polymerization.

Light cure resin systems are light sensitive compositions that contain catalysts that initiate polymerization upon receiving radiant energy such as light.

The preferred types of resins are acrylics/methacrylics because they are compatible with almost all contemporary dental resin systems currently on the market.

Resins such as epoxy, urethanes and other useful resins are also contemplated.

Useful acrylic resins are polyethylene glycol methacrylates, polypropylene glycol methacrylates, Diurethane dimethacrylate, hydroxyethyl methacrylate, bis-phenol A diglycidyl dimethacrylate, triethylenegycol dimethacrylate, isodecyl methacrylate, Bisphenol A ethoxylate dimethacrylates, Poly(ethylene glycol) methyl ether methacrylate, and many other useful methacrylic resins.

Light cure systems incorporate a tertiary amine such as dimethyl aminoethyl methacrylate and a photo initiator such as camphorquinone.

Chemical cure systems usually consist of benzoyl peroxide in part A, and dimethyl para toluidine in part B, that when mixed together initiate free radical polymerization.

The present invention may be embodied in other specific forms without departing from its spirit or essential characteristics. The described implementations are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed is:

1. A dental adhesive, comprising:

a polymer; and a dye or pigment; and wherein the dental adhesive is formulated to cure to form a bond that is weakened in response to the dye or pigment absorbing radiant energy at a wavelength of about 405 nm subsequent to curing.

2. The dental adhesive of claim 1, wherein the dye or pigment comprises at least one of a white dye, a white pigment, a translucent dye, and a translucent pigment.

3. The dental adhesive of claim 1, wherein the dye or pigment comprises at least one of 4,4"-(1,2-ethenediyl)bis-1,1'-biphenyl, and 4,4"-bis[(2-butyloctyl)oxy]-1,1':4',1":4"',1"''-quaterphenyl and 2-[1,1'-biphenyl]-4-yl-6-phenyl-benzoxazole and 3,5,3"''',5"''-tetra-t-butyl-p-sexiphenyl and 2-(1-naphthyl)-5-phenyl-oxazole and 3,5,3 . . . ,5 . . . -tetra-t-butyl-p-quinquephenyl.

4. The dental adhesive of claim 1, wherein the dye or pigment comprises at least one of a yellow dye and a yellow pigment.

5. The dental adhesive of claim 1, wherein the dye or pigment comprises 2,2"-([1,1'-biphenyl]-4.4'-diyldi-2,1-ethenediyl)bis-benzenesulfonic acid disodium salt.

6. The dental adhesive of claim 1, wherein the polymer comprises at least one of an acrylic and a methacrylic.

7. The dental adhesive of claim 1, wherein the polymer comprises at least one of polyethylene glycol methacrylates, polypropylene glycol methacrylates, Diurethane dimethacrylate, hydroxyethyl methacrylate, bis-phenol A diglycidyl dimethacrylate, triethylenegycol dimethacrylate, isodecyl methacrylate, Bisphenol A ethoxylate dimethacrylates, and Poly(ethylene glycol) methyl ether methacrylate.

\* \* \* \* \*